United States Patent
Kimmig et al.

[11] Patent Number: 6,166,383
[45] Date of Patent: Dec. 26, 2000

[54] NON-DISPERSIVE INFRARED GAS ANALYZER

[75] Inventors: Ludwig Kimmig, Ettlingen; Peter Krause; Michael Ludwig, both of Karlsruhe; Karlheinz Schmidt, Eggenstein-Leopoldshafen, all of Germany

[73] Assignee: Siemens AG, Munich, Germany

[21] Appl. No.: 09/123,034

[22] Filed: Jul. 27, 1998

[30] Foreign Application Priority Data

Aug. 27, 1997 [DE] Germany ............ 197 32 470

[51] Int. Cl.⁷ .................. G01J 5/08; G01N 21/61
[52] U.S. Cl. ............ 250/343; 250/344; 250/345; 250/349
[58] Field of Search ............... 250/343, 345, 250/349, 344

[56] References Cited

U.S. PATENT DOCUMENTS

| | | |
|---|---|---|
| 3,898,462 | 8/1975 | Ishida et al. |
| 5,055,688 | 10/1991 | Fabinski |
| 5,429,805 | 7/1995 | Uno et al. |
| 5,572,032 | 11/1996 | Fujiwara et al. |
| 5,693,945 | 12/1997 | Akiyama et al. |

FOREIGN PATENT DOCUMENTS

| | | |
|---|---|---|
| 967 633 | 10/1953 | Germany. |
| 25 05 006 C3 | 12/1977 | Germany. |
| 43 43 897 A1 | 12/1993 | Germany. |
| 44 03 763 A1 | 2/1994 | Germany. |
| 44 29 010 A1 | 2/1996 | Germany. |
| 196 01 873 A1 | 9/1996 | Germany. |

OTHER PUBLICATIONS

JP 5–215684 (A) in Patent Abstracts of Japan, P–1653, Dec. 3, 1993, vol. 17/No. 654.

*Primary Examiner*—Constantine Hannaher
*Assistant Examiner*—Andrew Israel
*Attorney, Agent, or Firm*—Kenyon & Kenyon

[57] ABSTRACT

A non-dispersive infrared gas analyzer for determining concentrations of carbon dioxide and/or carbon monoxide, hydrocarbons, and nitrogen oxides has two measuring cells 4, 6 consecutively traversed by a beam, with an optopneumatic detector 22 for carbon dioxide and an optopneumatic detector 23 for carbon monoxide arranged between them. Detectors 7, 8 for hydrocarbons and nitrogen oxides are arranged on the measuring cell 6 located downstream from detectors 22, 23 in the direction of the beam.

12 Claims, 1 Drawing Sheet

NON-DISPERSIVE INFRARED GAS ANALYZER

BACKGROUND OF THE INVENTION

1. Field of the Invention

The invention relates to an infrared gas analyzer for determining the concentrations of carbon dioxide, carbon monoxide, hydrocarbons, and nitrogen oxides in a sampled gas.

2. Description of Related Art

German Patent No. 967 633 describes a non-dispersive gas analyzer for determining carbon dioxide and carbon monoxide levels in a sampled gas. The gas analyzer operating by the dual beam principle has in each beam path a first measuring cell filled with sampled gas and traversed by an infrared beam, followed in sequence, in the direction of the beam, by an optopneumatic detector containing carbon monoxide, a second measuring cell filled with sampled gas, and an optopneumatic detector containing carbon dioxide.

From German Patent No. 39 37 141 A1 is known a non-dispersive infrared gas analyzer for determining levels of carbon dioxide, carbon monoxide, and methane, in which optopneumatic detectors are arranged in succession in the beam path downstream from the measuring cell, radiation filters being arranged between them, the detector immediately downstream from the measuring cell being filled with carbon monoxide, the next detector being filled with carbon dioxide, and the last detector being filled with methane.

Similarly, a non-dispersive infrared analyzer known from German Patent No. 25 05 006 C3 and U.S. Pat. No. 3,898,462 A has optopneumatic detectors, in the direction of the beam, downstream from the measuring cell, which in succession are filled with carbon monoxide, hydrocarbon, nitrogen oxide, and water vapor, respectively.

From German Patent No. 44 41 023 A it is known, in a non-dispersive infrared gas analyzer, to split a beam exiting from the measuring cell into a reflected and a transmitted partial beam using a beam splitter, the reflected partial beam being supplied to one detector for a certain gas component and the transmitted partial beam being supplied to another detector for another gas component or to another beam splitter. The beam splitter can be designed as an optical filter for the transmitted partial beam. Furthermore, the beam splitter can be arranged in a gas filter cell filled with an interfering gas.

In a similar infrared gas analyzer, known from German Patent No. 196 01 873 A1, an infrared beam is split into two partial beams by a beam splitter, the two components being passed through two different measuring cells filled with the sampled gas, and, upon exiting the measuring cells, being fed to different detectors for different gas components via additional beam splitters. In this context, the beam splitters are designed as optical filters for each transmitted partial beam.

An infrared gas analyzer known from German Patent No. A 44 03 763 has one single optopneumatic detector for determining the concentrations of a plurality of components such as carbon dioxide, carbon monoxide, and hydrocarbons in a sampled gas, the detector being filled with all the components to be analyzed. Filters are cyclically introduced in the path of the beam of the measuring cell that contains the sampled gas, an absorption range of one component falling within the passband range of each filter. On the basis of the detector output signals, which vary over time, the signal components to be associated with the individual gas components are determined, using signal analysis, as a function of the sequence in which the filters are introduced in the beam path.

In the aforementioned known gas analyzers, signal analysis is hindered by the fact that the individual components in the sampled gas not only absorb the infrared measuring light in different absorption ranges, but also do so with different intensities within those ranges. This is taken into account in the case of a non-dispersive infrared gas analyzer known from German Patent No. A 44 29 010 by passing the sampled gas through measuring cells of different lengths, each followed by an optopneumatic detector. Each detector contains one of the components to be analyzed, the length of the respective measuring cell being optimized to detect this component in the sampled gas. To pass the radiation through the parallel measuring cells, an infrared radiation emitter is made to pass by each measuring cell sequentially, making the construction of the gas analyzer relatively costly. The radiation cannot be passed through all the measuring cells simultaneously, since then each measuring cell would only receive a fraction of the total beam, which would no longer be sufficient for detection.

SUMMARY OF THE INVENTION

The object of the invention is to provide an infrared gas analyzer for determining the concentrations of carbon dioxide, carbon monoxide, hydrocarbons, and nitrogen oxides in a sampled gas having optimum detection characteristics in relation to the different absorptances of the individual components, its design being as simple as possible.

This object is achieved according to the present invention with a non-dispersive infrared gas analyzer for determining the carbon dioxide, carbon monoxide, hydrocarbon, and nitrogen oxide levels in a sampled gas 9

- having a first measuring cell 4 that can be filled with the sampled gas 9 and is traversed by an infrared measuring beam 3;
- having a radiation-transparent optopneumatic detector 22, containing carbon dioxide, arranged in the direction of the beam downstream from the first measuring cell 4,
- having a radiation-transparent optopneumatic detector 23, containing carbon monoxide, arranged in the direction of the beam downstream from the detector 22 containing carbon dioxide,
- having a second measuring cell 6 that can be filled with the sampled gas 9, arranged in the direction of the beam downstream from the detector 23 containing carbon monoxide, and
- having detectors 7, 8, 10, 11 arranged on the second measuring cell 6 for hydrocarbons and nitrogen oxides.

To further elucidate the invention, reference is made to the following drawings.

DETAILED DESCRIPTION OF THE PREFERRED EMBODIMENTS

Figure 1:
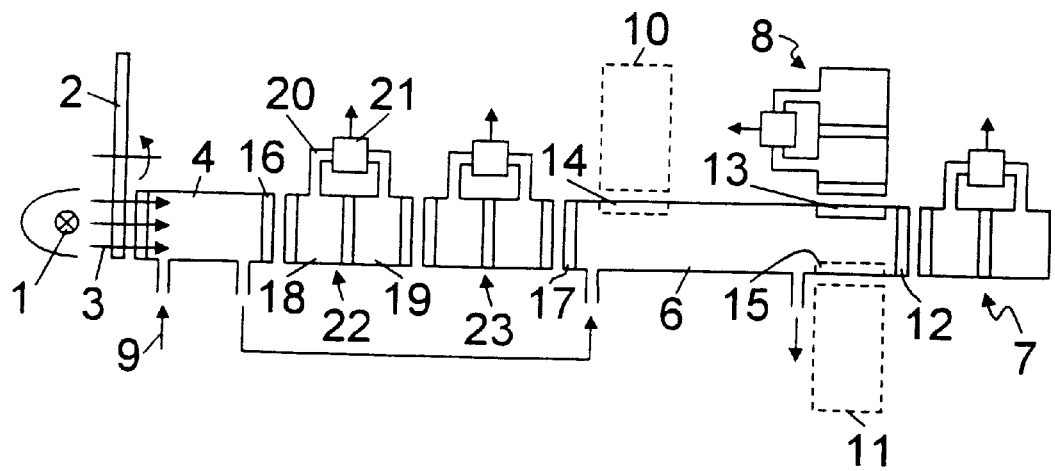
FIG. 1 shows an exemplary embodiment of the gas analyzer according to the present invention for determining carbon dioxide, carbon monoxide, hydrocarbon, and nitrogen oxide levels in a sampled gas.

FIG. 1 shows a non-dispersive infrared gas analyzer with an infrared radiation source 1, whose radiation is modulated using an orifice wheel 2. Modulated beam 3 passes through a first measuring cell 4 and enters two successive optopneumatic detectors 22 and 23. Optopneumatic detectors 22 and 23 are designed to let the radiation pass through, so that modulated beam 3, after passing through a second measuring cell 6 downstream from detector 23, arrives at two additional detectors 7 and 8, arranged on second measuring cell 6, located in this embodiment at its end region.

A sampled gas 9 to be analyzed is passed through the two measuring cells 4 and 6; the sampled gas here is an exhaust gas containing the components to be analyzed, carbon dioxide, carbon monoxide, nitrogen oxides, and hydrocarbons. For this purpose, the two measuring cells 4 and 6, with regard to their inlets and outlets, are connected either in parallel or in series. Optopneumatic detector 22 is used for detection of the carbon dioxide components in sampled gas 9 and is therefore filled with carbon dioxide. The subsequent optopneumatic detector 23 is used for detecting the carbon monoxide components and is therefore filled with carbon monoxide. The two detectors 7 and 8, which are also designed as optopneumatic detectors here, are used for detecting hydrocarbons and nitrogen oxides, respectively, in sampled gas 9, and are therefore filled with hydrocarbon and nitrogen oxide or appropriate substitute gases. Detectors 7 and 8 can also be filled with gas mixtures, for example, in the case of hydrocarbons, with methane and hexane, so that either the methane or the hexane component can be determined in sampled gas 9, in accordance with the application, using one and the same detector, on the basis of the different characteristic curves determined previously. For simultaneous detection of different hydrocarbons, e.g., methane and hexane, or different nitrogen oxides, e.g., nitrogen monoxide and nitrogen dioxide, other detectors 10, 11, here indicated with broken lines, can be provided on second measuring cell 6. Instead of optopneumatic detectors 7, 8, 10, and 11, detectors operating by other measuring principles can also be used.

In the embodiment shown, the second measuring cell 6, in its end region, has a window 12 situated transverse to the direction of the beam, downstream from which detector 7 is arranged, and a window 13 along the direction of the beam, downstream from which detector 8 is arranged. The amount of radiation incident in detector 8 is surprisingly high and is roughly on the same order of magnitude as the amount of radiation incident in detector 7. It is assumed that this is caused by the high degree of beam reflection on the inner wall of second measuring cell 6. The other detectors 10 and 11 are also arranged downstream from windows 14 and 15 of the second measuring cell, located along the direction of the beam, the distance between detectors 8, 10, 11 and the point where beam 3 enters the second measuring cell 6 being selectable as a function of the component to be analyzed in sampled gas 9 and its absorptance. Since the absorption ranges of individual components to be detected in sampled gas 9 may partially overlap, the individual windows 12 through 15, as well as outlet window 16 of the first measuring cell 4 and/or inlet window 17 of the second measuring cell 6 may be designed as optical radiation filters as needed in order to increase the selectivity of the gas analyzer.

Each of detectors 22, 23, 7, 8, 10, and 11 has, in a known manner, two successive radiation-transparent chambers, e.g., 18 and 19, which are connected via channel 20 to a pressure- or flow-sensitive sensor 21, which is located in the chambers and emits a detector signal. Due to the high absorptance of carbon dioxide and carbon monoxide, the first measuring cell 4 is relatively short, on the order of 5 mm, while the subsequent second measuring cell 6 is several times as long, e.g., 60 mm. Through the selected arrangement of detectors 22, 23, 7, 8, 10, and 11, filled with the different components, the detectors are prevented from influencing one another with their absorption ranges.

Beam 3 incident on the detectors, e.g., detector 22, causes pressure fluctuations due to absorption; the magnitude of these fluctuations is a function of the sampled-gas-specific pre-absorption of beam 3 in the upstream measuring cells 4 and 6. Whereas the radiation of the center and edges of the absorption line of the gas component to be determined is absorbed in the gas layer of the respective first detector chamber 18, the radiation of the line edges is mostly absorbed in the subsequent gas layer of second detector chamber 19, so that pressure differences detected by sensor 21 appear between the two detector chambers 18 and 19.

Figure 2:
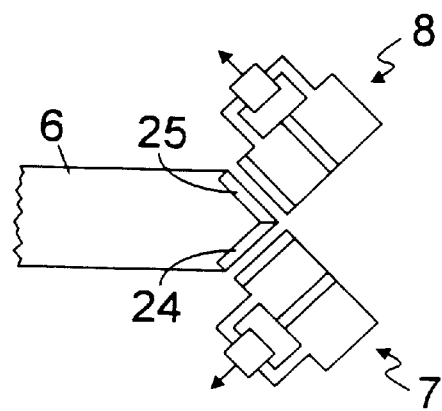
FIG. 2 shows an alternative arrangement of detectors for determining hydrocarbon and nitrogen oxide levels.

In the exemplary embodiment according to FIG. 2, the end region of the second measuring cell 6 has two windows 24 and 25, at an angle to the direction of the beam, detectors 7 and 8 being arranged downstream from these windows.

What is claimed is:

1. A non-dispersive infrared gas analyzer for determining the carbon dioxide, carbon monoxide, hydrocarbon, and nitrogen oxide levels in a sampled gas, comprising:
   a first measuring cell that can be filled with the sampled gas and is traversed by an infrared measuring beam;
   a radiation-transparent optopneumatic detector containing carbon dioxide, arranged in the direction of the beam downstream from the first measuring cell;
   a radiation-transparent optopneumatic detector containing carbon monoxide, arranged in the direction of the beam downstream from the detector containing carbon dioxide;
   a second measuring cell that can be filled with the sampled gas, arranged in the direction of the beam downstream from the detector containing carbon monoxide;
   at least one detector for detecting hydrocarbon arranged on the second measuring cell; and
   at least one detector for detecting nitrogen oxide arranged on the second measuring cell.

2. The non-dispersive infrared gas analyzer according to claim 1, wherein the at least one detector for detecting hydrocarbon and the at least one detector for detecting nitrogen oxide are optopneumatic detectors.

3. The non-dispersive infrared gas analyzer according to claim 1, wherein the length of the second measuring cell is greater than the length of the first measuring cell.

4. The non-dispersive infrared gas analyzer according to claim 3, wherein the second measuring cell has a length that is more than ten times greater than the length of the first measuring cell.

5. The non-dispersive infrared gas analyzer according to claim 2, wherein the length of the second measuring cell is greater than the length of the first measuring cell.

6. The non-dispersive infrared gas analyzer according to claim 5, wherein the second measuring cell has a length that is more than ten times greater than the length of the first measuring cell.

7. The non-dispersive infrared gas analyzer according to claim 1, wherein the second measuring cell has at least two windows, downstream of each of which is arranged one of the at least one detector for detecting hydrocarbon and the at least one detector for detecting nitrogen oxide, and wherein at least one of the at least two windows is arranged along the direction of the beam.

8. The non-dispersive infrared gas analyzer according to claim 2, wherein the second measuring cell has at least two windows, downstream of each of which is arranged one of the at least one detector for detecting hydrocarbon and the at least one detector for detecting nitrogen oxide, and wherein at least one of the at least two windows is arranged along the direction of the beam.

9. The non-dispersive infrared gas analyzer according to claim 7, wherein one of the at least two windows is arranged transverse to the direction of the beam.

10. The non-dispersive infrared gas analyzer according to claim 8, wherein one of the at least two windows is arranged transverse to the direction of the beam.

11. The non-dispersive infrared gas analyzer according to claim 1, wherein the second measuring cell has at least two windows, downstream of each of which is arranged one of the at least one detector for detecting hydrocarbon and the at least one detector for detecting nitrogen oxide, and wherein at least one of the at least two windows is arranged at an angle to the direction of the beam.

12. The non-dispersive infrared gas analyzer according to claim 2, wherein the second measuring cell has at least two windows, downstream of each of which is arranged one of the at least one detector for detecting hydrocarbon and the at least one detector for detecting nitrogen oxide, and wherein at least one of the at least two windows is arranged at an angle to the direction of the beam.

* * * * *